(12) United States Patent
Tuma

(10) Patent No.: US 8,945,130 B2
(45) Date of Patent: Feb. 3, 2015

(54) TOOL ATTACHMENT FOR MEDICAL APPLICATIONS

(75) Inventor: Gregor Tuma, München (DE)

(73) Assignee: Brainlab AG, Feldkirchen (DE)

( * ) Notice: Subject to any disclaimer, the term of this patent is extended or adjusted under 35 U.S.C. 154(b) by 390 days.

(21) Appl. No.: 12/793,967

(22) Filed: Jun. 4, 2010

(65) Prior Publication Data

US 2010/0312247 A1  Dec. 9, 2010

Related U.S. Application Data

(60) Provisional application No. 61/233,519, filed on Aug. 13, 2009.

(30) Foreign Application Priority Data

Jun. 5, 2009 (EP) ..................... 09162034

(51) Int. Cl.
| | | |
|---|---|---|
| *A61B 17/58* | (2006.01) | |
| *A61B 17/16* | (2006.01) | |
| *A61B 17/17* | (2006.01) | |
| *A61B 19/00* | (2006.01) | |
| *A61F 2/36* | (2006.01) | |

(52) U.S. Cl.
CPC .......... *A61B 17/1668* (2013.01); *A61B 17/175* (2013.01); *A61B 2019/505* (2013.01); *A61B 2019/5255* (2013.01); *A61B 2019/5268* (2013.01); *A61F 2/3603* (2013.01)
USPC .............................. 606/79; 606/86 R; 606/89

(58) Field of Classification Search
USPC ............ 600/414, 424, 426; 606/79–85, 86 R, 606/91, 96, 130, 167–184, 88, 89; 623/22.12, 22.15, 32; 408/79–80; D24/133–155, 158; 409/178–179; 144/387, 392, 394, 402, 420; 29/407.01, 407.05; 388/937
IPC ....................................................... B32Q 9/02
See application file for complete search history.

(56) References Cited

U.S. PATENT DOCUMENTS

| | | | |
|---|---|---|---|
| 2005/0119639 A1* | 6/2005 | McCombs et al. ................. | 606/1 |
| 2005/0192584 A1* | 9/2005 | Walker et al. .................... | 606/79 |
| 2005/0234332 A1 | 10/2005 | Murphy | |
| 2005/0234465 A1 | 10/2005 | McCombs et al. | |
| 2008/0009697 A1 | 1/2008 | Haider et al. | |

FOREIGN PATENT DOCUMENTS

WO   2006/100458   9/2006

* cited by examiner

*Primary Examiner* — Todd Manahan
*Assistant Examiner* — Eric S Gibson
(74) *Attorney, Agent, or Firm* — Tucker Ellis LLP

(57) ABSTRACT

The present invention relates to a tool attachment for medical applications, comprising: a connecting section which is at rest relative to the part of the bone while the part of the bone is being machined; at least one machining section for machining a part of the bone; a fastening facility for fastening the tool attachment to a control device, wherein the connecting section is designed to connect the tool attachment, such that it is stationary, to a tool attachment guide.

11 Claims, 5 Drawing Sheets

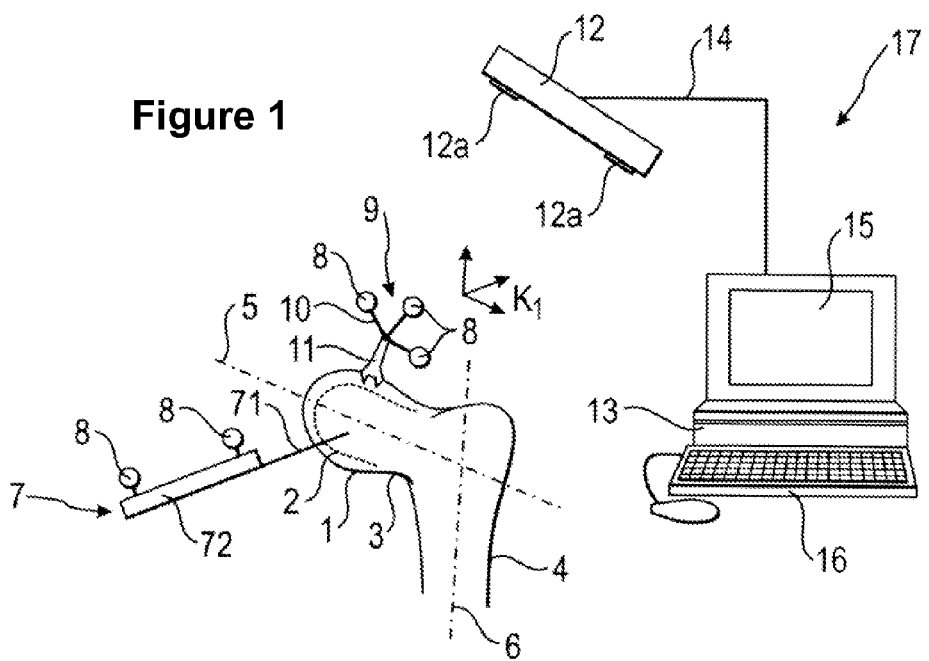
Figure 1
Figure 2
Figure 2a
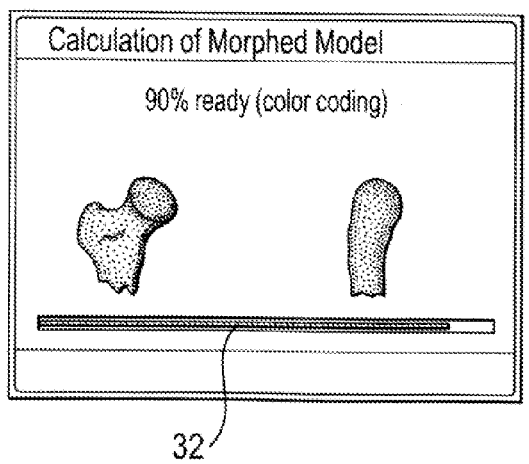
Figure 2b
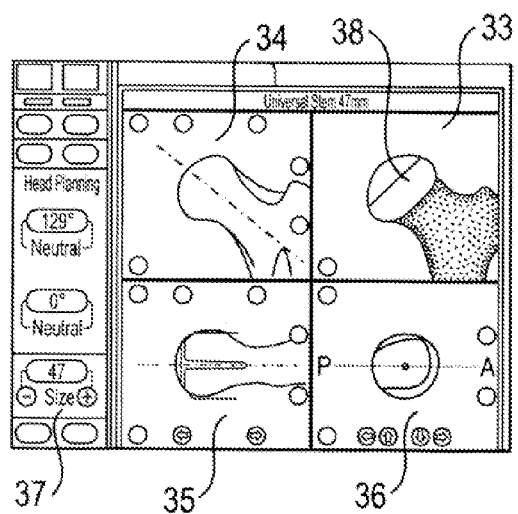

TOOL ATTACHMENT FOR MEDICAL APPLICATIONS

RELATED APPLICATION DATA

This application claims the priority of U.S. Provisional Application No. 61/233,519, filed on Aug. 13, 2009, which is hereby incorporated in its entirety by reference.

FIELD OF THE INVENTION

The present invention relates to a tool attachment for medical applications, in particular for machining parts of bones.

BACKGROUND OF THE INVENTION

More recent developments in surgery and/or orthopedics have led to the design of prosthetic femoral caps for which, when they are inserted into the body of a patient, only the surface and/or exterior layer of the femoral head (caput femoris) is removed and replaced with a metal cap. This method for removing the surface of the bone ("resurfacing") differs from the conventional methods in that the femoral head has hitherto been simply sawn off and replaced entirely with a prosthetic shaft. Resurfacing has hitherto been completed manually, i.e. the apparatus for removing—in particular, fraising off—the surface of the bone has been manually guided by a surgeon, wherein this has resulted in major uncertainties due to a movement of the fraising drill relative to the femur.

When fraising the surface of the bone in the hitherto usual way, so-called "femoral notching" has occurred: by manually guiding the fraising head, it is possible to inadvertently fraise a notch into the femoral neck, which can lead to a fracture of the femoral neck when a load is post-operatively placed on the hip joint.

SUMMARY OF THE INVENTION

It is an object of the invention to enable an improvement in machining the surface of a bone using a tool attachment. This object is solved by the teaching of the independent patent claims, wherein the dependent claims relate to particular embodiments of this teaching. The features of different embodiments can be combined with each other.

The invention provides a fraising head which can be coupled to a fraising head holder—in particular, a fraising head guide—which is attached in the femoral neck. The fraising head holder (for example, a fastening shaft) which is attached in the femoral neck can in particular comprise a reference star holder, such that the fraising head coupled to it has a sufficiently exact position, in accordance with a plan for the operation, in order to machine the bone at the desired point. Guiding the fraising head automatically, in particular in accordance with a control program (i.e. in a controlled way), is enabled.

The present invention relates to a tool attachment for medical applications, in particular for fraising and/or drilling and/or cutting parts of bones. Within the framework of this invention, "fraising" is understood to mean a chipping or grinding method for machining surfaces, in particular surfaces of a bone. "Drilling" is intended to denote a method in which a depression and/or channel and/or hole is worked into a bodily structure, in particular a bone. "Cutting" parts of bones is understood to mean a mechanical separating method by which a part of a bone is divided into a number of parts, but at least two parts, of the bone. The tool attachment in accordance with the invention comprises at least one machining section for machining, i.e. fraising and/or drilling and/or cutting, a part of a bone. Fraising can in particular be performed in such a way that a femoral head is fraised along a surface which is rotationally symmetrical about the longitudinal axis of the femoral head. The femoral head is cited here as an example of any body structures, in particular parts of bones (for example, condyles, shoulder blade, etc.). To this end, the machining section comprises for example a fraise such as is commonly used for surgically machining bones. This fraise can in particular be configured such that it fraises the surface of the femoral neck along a rotationally symmetrical surface. The rotationally symmetrical surface can represent a surface of a rotationally symmetrical geometric figure (elementary geometric shape) which is rotationally symmetrical with respect to a longitudinal axis of the femoral head. A cylindrical shell and/or a conical surface (conical shell) are for example possible in this respect. A combination of a cylindrical shell and a conical shell can also be produced in accordance with the invention: the proximal end of the femoral head can for example be fraised such that it tapers, i.e. conically, wherein a cylindrical shape of the remaining femoral head and/or femoral neck in its machined form is connected distally to the base of the cone. Fraising in accordance with the invention by means of a tool attachment which is guided by a robot in a surgical navigation method (image-guided surgery or IGS) enables surfaces to be machined exactly. In this way, a rotationally symmetrical shape of the femoral neck, in particular one of the aforesaid elementary shapes, is created. The machining section and/or fraise can thus be configured such that it rotates on a surface of the elementary shape, the longitudinal axis of which lies on and/or parallel to the longitudinal axis off the femoral neck, i.e. the machining section fraises a surface of the femoral neck which, at the end of machining the bone, lies on a surface, in particular a shell surface, of such an elementary shape. Such a shell surface is thus rotationally symmetrical about the longitudinal axis of the femoral head and/or about an axis which is parallel to the longitudinal axis of the femoral head. The longitudinal axis of the femoral head is in particular understood to mean an axis along which the femoral head exhibits rotational symmetry and/or approximate rotational symmetry. The tool attachment also comprises a fastening facility for fastening the tool attachment to a control device which guides (directs) and/or drives the tool attachment, i.e. the control device in particular controls the spatial location of the tool attachment. This fastening facility for example ensures—by way of a positive-fit and/or force-fit and/or material-fit mechanical connection to the control device—that the tool attachment can be guided in a controlled way. The control device can for example comprise the arm of a robot, wherein the robot can be controlled manually by a user and/or via a computer program. The control device can also comprise a manual grip for manually guiding the tool attachment, in order that the tool attachment can be manually guided by a machining worker to and/or away from a machining position of the tool attachment in which the femoral head is to be machined. The location of the tool attachment can then be finely or roughly controlled, i.e. controlled in the closer vicinity of the femoral head and/or part of the body to be machined, with the aid of the control device. The control device can comprise a motor (for example, an electric motor) and/or a transmission for driving the tool attachment. It is thus for example possible to control a robot such that it moves the tool attachment to positions which are ascertained by a surgical navigation method. To this end, a marker device is attached to the control device and/or the tool attachment. The positions can be ascertained in such a way that a surface of the femoral head is measured off (registered) using a pointing apparatus (pointer), before machining. Measuring off patient-specific points/landmarks on the surface of an actual bone with a pointer is referred to as "registering". The tool attachment is then controlled relative to the surface to be machined by comparing the ascertained position of the control device and/or tool attachment and the (in particular registered) location (i.e. spatial position and orientation) of the surface to be machined.

A pointer is a rod comprising one or more—advantageously, two—markers fastened to it, wherein the pointer can be used to measure off individual coordinates, in particular spatial coordinates (i.e. three-dimensional coordinates), on a part of the body, for example within the framework of a registering method, wherein a user guides the pointer (in particular, a part of the pointer which has a defined and advantageously fixed location with respect to the at least one marker which is attached to the pointer) to the position corresponding to the coordinates, such that the position of the pointer can be determined by detecting the marker on the pointer using a surgical navigation system. The relative location between the markers of the pointer and the part of the pointer used to measure off coordinates (in particular, the tip of the pointer) is in particular known. The surgical navigation system then enables the position (the three-dimensional coordinates) to be assigned to a predetermined body structure, wherein the assignment can be made automatically or by user intervention.

The position and shape of the femoral head are thus preferably known before it is machined using the tool attachment in accordance with the invention, and corresponding data is transmitted to a data processing device, where it is for example also stored, wherein the data processing device consists of a computer, i.e. in particular a chip and/or processor, a storage unit and as applicable an indicating device (such as a monitor and/or an acoustic transmitter such as for example a loudspeaker). Within the framework of the invention, another marker device which can comprise one or more individual marker devices and/or a reference star is attached to an instrument which is connected stationary to the femoral head, in particular the fraising head guide, for navigation during an operation.

A marker device can be a reference star, a pointer and/or an individual marker or a number of markers.

It is the function of a marker to be detected by a marker detection device (for example, a camera or an ultrasound receiver), such that its spatial location (i.e. position and/or alignment) can be ascertained. Such markers can be active markers. An active marker emits for example electromagnetic radiation and/or waves, wherein said radiation can be in the infrared, visible and/or ultraviolet spectral range. The marker can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also however exhibit a cornered—for example, cubic—shape.

A "reference star" refers to a device with a number of markers, advantageously three markers, attached to it, wherein the markers are attached to the reference star such that they are stationary and advantageously detachable, thus providing a known (and advantageously fixed) location of the markers relative to each other. The location of the markers relative to each other can be individually different for each reference star used within the framework of a surgical navigation method, in order to enable the corresponding reference star to be identified by a surgical navigation system on the basis of the location of the markers relative to each other. It is therefore also then possible for the objects (for example, instruments and/or parts of the body) to which the reference star is attached to be identified and/or differentiated. In a surgical navigation method, the reference star serves to attach a plurality of markers to an object (for example, a bone or a medical instrument) in order to be able to detect the spatial location of the object (i.e. its position and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to. Where it is clear from the context, the term "reference star" can also refer to a reference star together with at least one marker attached to it. Such a system consisting of a reference star and at least one marker can also be referred to as a marker star.

A "marker holder" is understood to mean a way of attaching an individual marker, which serves to attach the marker to an instrument, a part of the body and/or a holding element of a reference star, wherein the attachment can be stationary and advantageously detachable. The shape of a marker holder can for example be rod-shaped and/or cylindrical. A way of fastening the marker device (such as for example a latch mechanism), which assists in seating the marker device on the marker holder in a force fit and/or positive fit, can be provided at the end of the marker holder which faces the marker.

A first marker device (also referred to in the following as a "bone marker device") is attached in a position which is fixed relative to the femoral head. This can be achieved by directly mechanically fastening the bone marker device to the bone or by fastening the bone marker device to a connector piece which is fixedly and mechanically connected to the bone. The mechanical connections which arise within this context are preferably detachable. The connector piece preferably assists in seating the bone marker device such that it is stationary relative to the part of the bone to be machined.

A second marker device is preferably attached stationary to the control device, in particular to a first robot arm. Such a marker device is also referred to here as a robot marker device. The first robot arm can be navigated and/or moved relative to the femoral head with the aid of the robot marker device, such that it is possible to insert a tool attachment guide—in particular a fraising head guide which is guided on the first robot arm and the position of which relative to the robot marker device is known beforehand and preferably fixed—along the longitudinal axis of the femoral head and/or femoral neck, into the bone. As an alternative to or in addition to the robot marker device, a marker device can be attached to the fraising head guide; this alternative or additional marker device is then referred to as a guide marker device or fraising head guide marker device. In the following, a fraising head guide is cited as an example of a tool attachment guide which can be fastened to a part of a bone. It is however also possible in accordance with the invention to use other tool attachment guides, in particular guides for drilling and/or cutting attachments.

The fraising head guide allows the tool attachment to be (detachably) mechanically connected (in particular coupled) to the fraising head guide, such that a fixed mechanical connection (which is in particular stationary and/or detachable)

between the tool attachment and the femoral head—mediated by the fraising head guide—results. This assists and in particular ensures that during machining, the position of the tool attachment is fixed relative to the femoral head and/or the surface to be machined, in particular even when the surface to be machined is spatially moved, wherein the fraising head guide is preferably configured such that when it is connected to the tool attachment, the movements (for example, rotation) of the at least one machining section which are necessary for machining the femoral head are not impeded.

The guide marker device is preferably mechanically fastened, such that it is stationary and/or detachable, to the fraising head guide during the movement and/or insertion procedure. It is thus possible to use a marker device for jointly navigating the fraising head guide and the robot arm, if the fraising head guide has a fixed position relative to the robot arm. This can also be the case if the fraising head guide is mechanically connected (for example via a plug connection and/or a screw connection, i.e. in a positive fit and/or in a force fit) to the robot arm such that it is detachable but stationary. The guide marker device can thus, if desired, replace the robot marker device for the aforesaid purpose.

Once the fraising head guide has been inserted into the femoral head, such that it assumes a stationary location relative to the femoral head, a second robot arm (which can be identical to the first robot arm which in particular comprises the robot marker device) on which the tool attachment in accordance with the invention is placed can be navigated relative to the fraising head guide and/or the guide marker device, in particular by detecting the robot marker device and the guide marker device, such that the machining section is and/or can be applied to the bone in a position which is suitable for rotationally symmetrically, in particular cylindrically, fraising the femoral head. The robot arm can be moved by being connected to a movement unit. Said movement unit can for example be a motor, in particular an electric motor, which receives control signals from a computer, in particular the computer of the surgical navigation system, and relays them to the robot arm via a movement mechanism.

When the machining section is applied to the bone, the guide marker device is preferably still fastened to the fraising head guide. In order for the tool attachment to be able to enter into the mechanical connection with the fraising head guide as described above, a cavity for inserting a marker device can be provided on the tool attachment. The marker device is advantageously the guide marker device, which is preferably attached to the fraising head guide such that it is stationary relative to the fraising head guide. The cavity in particular assists in seating the tool attachment, such that it is detachable and stationary, relative to the guide marker device. The cavity can be molded into a surface of the tool attachment as a depression. It can however also be formed as a channel through the tool attachment, in order to enable the guide marker device to be inserted. The cavity advantageously has the shape of a slot in the tool attachment which extends parallel to a longitudinal axis and/or rotational axis (in particular, a cylindrical axis) of the tool attachment. The cavity and the guide marker device (in particular, a holding element of the guide marker device) are advantageously designed such that they are at least partially congruent with respect to each other. This assists in fixedly seating the tool attachment mechanically on the guide marker device, in particular in a positive fit. It is advantageously seated such that it is detachable. It is equally possible in accordance with the invention to design the cavity such that it is at least partially congruent with respect to the fraising head guide. This assists in fixedly seating the tool attachment mechanically on the fraising head guide, in particular in a positive fit, by means of the cavity, if a component of the fraising head is also inserted into the cavity, in particular in addition to a component of the guide marker device. This enables the tool attachment to be seated on the guide marker device and/or the fraising head guide with zero clearance; in particular, a rotationally fixed and advantageously detachable connection between the tool attachment and the guide marker device and/or fraising head guide is established and/or assisted. The slot is advantageously open where it points in the direction of the femoral head, such that a bone marker device arranged on the femoral head or a guide marker device can be moved in the tool attachment and/or inserted into the tool attachment during the applying procedure. The cavity can be molded into a supporting section and/or a machining section of the tool attachment.

The supporting section of the tool attachment refers here to a resting part, in particular a part of the tool attachment, which is fastened to and bears the machining section. The supporting section in particular comprises a connecting section. The supporting section is in particular at rest relative to the part of the bone while the part of the bone is being machined, i.e. it exhibits a stationary behavior relative to the part of the bone. The connecting section serves to mechanically connect the tool attachment, such that it is stationary and advantageously detachable, to the fraising head guide. The connecting section can for example comprise a molding into the supporting section, which is advantageously designed such that it is at least partially congruent with respect to the shape of the fraising head guide. This enables and/or assists a fixed, mechanical—in particular positive-fit—connection between the tool attachment and the fraising head guide. A coupling mechanism, such as for example a latch mechanism, which is arranged on the connecting section and engages with and/or latches into a corresponding counter part on the fraising head guide is also possible in accordance with the invention. This advantageously establishes and/or assists a zero-clearance seating, in particular a rotationally fixed connection between the tool attachment and the fraising head guide.

The cavity is advantageously only molded into the supporting section, wherein the supporting section preferably protrudes in the direction of the open end of the tool attachment, which in the operational state points in the direction of the femoral head and in particular away from the robot arm, beyond the at least one machining section in the longitudinal direction of the tool attachment. The cavity is preferably situated in a region of the supporting section which during machining is situated outside a movement and/or machining region of the at least one machining section. This enables the guide marker device which protrudes into the cavity to remain in its position during machining. The tool attachment can then encompass the guide marker device, and at least the supporting section can have a fixed relative position with respect to it, wherein the guide marker device is simultaneously situated outside the movement region of the at least one machining section. The presence of the guide marker device is therefore not an obstacle to operating the at least one machining section, and damage both to a machining section and to the guide marker device during machining thus becomes less likely. A molding which assists in seating the tool attachment on the guide marker device in an exact fit can be provided at an end of the cavity, in particular the slot, which faces the robot arm. This can for example be a round and/or graduated circular and/or semi-circular shape and/or a shape which is cornered and/or polygonal at least in sections, in particular in a projection onto a plane, wherein the plane lies perpendicular to the longitudinal direction of the holding element of the guide marker device if the latter is a reference star (and/or perpendicular to the longitudinal direction of the marker holder if the marker device is an individual marker). The molding can thus be designed at least partially in an exact fit with respect to the holding element and/or the reference star. A snap-in mechanism (latch mechanism) can also be provided on the cavity, which engages with a corresponding surface shape of the guide marker device and/or the fraising head guide. Conversely, a latch mechanism can also be provided on the guide marker device and/or the fraising head guide, which engages with a corresponding surface shape of the cavity. In particular, elements can be provided at the end of the cavity facing the robot arm which assist in seating the tool attachment on the guide marker device in a force fit—for example, springs and/or clamps.

Advantageously, the connecting section assists in seating the at least one machining section, such that it is stationary, relative to the femoral head by being in contact with the guide marker device and/or the fraising head guide. In accordance with one embodiment, the connecting section is provided for fixedly, mechanically and detachably connecting to the fraising head guide. This connecting section can be provided as an alternative to or in addition to the aforesaid cavity provided in the machining section. The cavity can also be provided in the connecting section, as described above. Thus, in accordance with one embodiment, the connecting section can at least partially comprise the cavity. This is particularly advantageous if a detachable mechanical connection between the tool attachment and a component of the guide marker device is to be established. For if the guide marker device and the fraising head guide are mechanically connected to each other in a sufficiently stable way, it is possible to dispense with establishing a direct detachable mechanical connection between the connecting section and the fraising head guide in order to machine the part of the bone.

The connecting section is advantageously arranged in and/or on a longitudinal axis of the tool attachment such that during machining, it lies opposite the part of the fraising head guide which protrudes out of the bone and/or is exposed. In accordance with one embodiment, a stable connection of the connecting section—by the connecting section preferably blocking at least a lateral displacement of the tool attachment relative to the machining plane and/or radially with respect to the longitudinal axis of the tool attachment—enables the supporting section, which preferably comprises the connecting section or is at least connected stationary to it, to be seated, such that it is stationary, relative to the part of the bone to be machined. In particular, the connecting section is at rest, during machining, relative to the part of the bone to be machined. The longitudinal axis of the tool attachment is in particular to be understood to mean an axis along which the tool attachment exhibits rotational symmetry and which is preferably placed parallel to and/or on the longitudinal axis of the femoral head when the bone is machined. In accordance with another embodiment, a connection which serves the same purpose can also be established between the connecting section and the guide marker device. The connecting section can be arranged in and in particular on the supporting section. The connecting section can comprise a recess and/or depression and/or a connecting part which can enter into a mechanical connection, in particular a positive-fit and/or force-fit mechanical connection, with the fraising head guide. Said connecting part can for example comprise a snap lock and/or a snap-in mechanism and/or latch mechanism. Said connecting part is preferably arranged at a point on the tool attachment which in the machining position lies in particular opposite an end piece of the fraising head guide and/or a connector piece arranged on the fraising head guide. Said connector piece functions for example as an adaptor between the fraising head guide and the tool attachment and advantageously protrudes out of the bone and is situated on and/or near the longitudinal axis of the femoral head, i.e. in particular runs along and/or parallel to the longitudinal axis. The fixed mechanical connection between the tool attachment and the fraising head guide and/or the guide marker device enables the surface of the femoral head to be machined and/or fraised in an exact shape and assists in precisely machining the femoral neck in accordance with a plan for an operation. The connecting section can for example comprise a round and/or circular and/or also polygonal and/or cornered depression on a surface of the supporting section which faces the femoral head. This depression can enter into a connection, which is at least partially in an exact fit and/or in a positive fit and/or in a force fit, with the opposite part (which is advantageously not countersunk in the bone) of the fraising head guide (for example, the connector piece), for which purpose said part of the fraising head guide advantageously has a shape which represents a negative of the depression. The surface shape (topography) of the opposite part of the fraising head guide (in particular the connector piece) is thus configured such that it can engage—flush and/or in a positive fit—with the oppositely shaped surface shape (topography) of the connecting section. It is however also possible to mould a depression into the part of the fraising head guide which protrudes out of the bone (i.e. the part of the fraising head guide which is exposed and is not countersunk in the bone—in particular, the connector piece), which is for example configured to be annular and/or circular and/or also polygonal and/or cornered. It is then expedient if the supporting section comprises a protrusion which can engage with the depression on the exposed part of the fraising head guide, in particular in an exact fit and/or with zero clearance and/or rotationally fixed, when the tool attachment is applied to the fraising head guide. If the connecting section comprises a depression and/or protrusion which is embodied to be round and/or circular, then an indentation and/or notch in the exterior line of the depression and/or protrusion can engage with a corresponding negative on the opposite part of the fraising head guide, in order to prevent the tool attachment from twisting relative to the fraising head guide and/or the femoral head. It is however also possible in accordance with the invention for a polygonal protrusion to be molded on the side of the tool attachment and for a depression in the form of the corresponding negative to be molded on the exposed part of the fraising head guide. This makes it more difficult for the robot arm and/or a supporting section to torque and/or twist relative to the femoral head during machining and/or fraising. In addition to the protrusions and depressions (but also independent of their presence), a snap lock and/or latch mechanism can also be arranged on the connector piece, in order to increase the stability of the connection between the tool attachment and the fraising head guide. Additionally or alternatively, a snap lock and/or latch mechanism can be arranged on the connecting section, in order to assist in a detachable, fixed, mechanical connection between the connecting section and the connector piece. The connector piece thus has in particular the function of a coupling between the tool attachment and the fraising head guide.

The cavity can be molded into at least one machining section and simultaneously into the supporting section and/or the connecting section. The cavity runs for example radially from the outside inwards, for example from the supporting section to the connecting section via a machining section, in order to accommodate at least the holding element of a guide marker device. It can however also be molded into at least one machining section only or into the connecting section only. Once the tool attachment has been coupled to the fraising head guide, but before machining, the guide marker device is then removed in accordance with one embodiment, in order to not represent an obstacle in the movement region of a machining section if the guide marker device is provided in the movement region of the machining sections and/or on a machining section.

The cavity advantageously exhibits dimensions and/or a width which in particular enable a part of a marker device to be guided through it. Said part of the marker device can for example be a holding element of a reference star. In this case, the slot is in particular wide enough that the holding element can be guided through the slot, along the longitudinal extension of the slot. In particular, the longitudinal direction of the holding element forms a right angle with the longitudinal plane of the slot as the holding element is guided through the slot.

The location of the cavity can be adjustable relative to the tool attachment (in particular, relative to the supporting section). A slot-shaped cavity can for example be arranged in a part of the tool attachment which can be shifted relative to other components of the tool attachment. The slot can thus for example be arranged in a plate which is inserted into the supporting section and/or the machining section, coplanar with a surface of the supporting section and/or a machining section and/or the connecting section, and can be shifted within the supporting section and/or connecting section and/or machining section. This enables the cavity to be adjusted exactly to the position of the guide marker device which is to be inserted into it, while being simultaneously independent of for example particular bone shapes. It is thus also possible to apply the cavity to the marker device, if the part of the bone to be machined exhibits a geometry which is difficult to encompass using the tool attachment.

It is possible in accordance with the invention to configure parts of the supporting section to be deflectable with respect to a machining configuration, such that two mutually opposite parts of a supporting section can in particular be guided around the marker device and/or the holding element while the tool attachment is applied to the femoral head, wherein the "machining configuration" refers to a geometric adjustment of the tool attachment and/or its components which is advantageous when machining the bone. The "machining configuration" is to be distinguished from the "machining position" which describes the location of the tool attachment which enables machining in a machining configuration relative to the part of the bone to be machined. It is thus possible to pivot one part of the supporting section relative to another part of the supporting section, in particular to pivot the former away from the latter, in order to create a gap into which the guide marker device can be inserted. Once at least a part of the guide marker device has been inserted into the gap, the supporting section can be closed again (i.e. its parts which were previously pivoted away from each other are converged towards each other), until it at least partially surrounds the guide marker device. This configuration comprising closed supporting sections is then a component of a machining configuration. In this case, the cavity can comprise two semi-circular recesses in the supporting section, wherein one of the recesses is arranged on one of the two pivotable parts of the supporting section, respectively, wherein the two recesses are in particular arranged such that they lie opposite each other when the supporting section is closed, such that they form a hole and/or channel in which at least a part of the marker device can lie, wherein it is advantageous if the cavity (in particular, the channel) terminates at least partially in an exact fit and/or in a positive fit with the guide marker device, in order to assist in positioning the tool attachment exactly and/or such that it is stationary, relative to the guide marker device.

The cavity preferably allows the tool attachment to be applied exactly to the guide marker device in a position which represents a desired position for fraising, such that a predetermined and known relative location between the guide marker device and the tool attachment is set, in particular when the guide marker device and the cavity are in contact in an exact fit. The position of the tool attachment (once applied) is ascertained in a surgical navigation method by comparing the ascertained position of the robot arm and/or a robot marker device, the locations of which are respectively known and preferably fixed relative to the tool attachment, with the ascertained position of the guide marker device and/or by combining this comparison with the registered shape of the femoral head and/or geometric data of the femoral head which is known before the operation. The prior-known data of at least parts of the patient's body can for example be obtained using medical imaging methods and is preferably provided to the method in accordance with the invention. Such a method is advantageously understood to mean apparatus-based methods in radiology, such as for example computed tomography (CT), x-ray tomography, magnetic resonance tomography (MRT and/or MRI), conventional x-ray, sonography and/or ultrasound examinations, and positron emission tomography. Where data is "provided", this means that it is ready for use by the method in accordance with the invention. The data can achieve this state of "being ready" by for example being captured (for example by analysis apparatuses) or by being input (for example via interfaces). The data can also have this state by being stored in a memory (for example a ROM, CD and/or hard drive) and thus ready for use within the framework of the method in accordance with the invention. The data can also be determined, in particular calculated, in a step of the method in accordance with the invention before being provided, in particular before being stored.

The position of the machining section relative to the bone (the machining position) which is suitable for machining and/or fraising can be defined such that the machining section at least partially encompasses the femoral head, in particular along and/or parallel to its longitudinal axis. If a tool attachment is hollow-cylindrical, the femoral head is at least partially encompassed coaxially by the machining section. It is however also possible in accordance with the invention for the femoral head to be at least mostly encompassed by the machining section, in particular along and/or parallel to the entire length of its longitudinal axis and/or from one end of its longitudinal axis to the other. "Encompassed" is understood here to mean that the surface of the bone lies opposite a machining section, at least in sections, in at least two and advantageously more directions, i.e. a section of the surface of the bone preferably lies opposite each machining section in the interior of the hollow-cylindrical tool attachment.

The tool attachment can also have a forcipate shape. The machining sections can then be arranged on at least one arm of the forcipate shape which is mounted such that it can be moved in the tool attachment and rotates about the femoral head in order to move the machining section into the machining position. In this case, the supporting section can be arranged in a hollow-cylindrical shape about the at least one arm. The supporting section can however also be designed such that it is planar and/or cuboid, parallel to the longitudinal axis of the femoral head. The supporting section can however also be worked into an arm and/or comprised by an arm. The supporting section can also encompass only a part of the femoral head and in particular not surround it rotationally symmetrically during machining. It is advantageous if the supporting section is situated outside the movement region of the at least one machining section, such that the movement of the machining section (in particular during machining) is not impeded by the arrangement of the supporting section.

In order that the femoral head can be machined rotationally symmetrically, advantageously in a cylindrical shape, a tool attachment which is for example hollow-cylindrical advantageously comprises a recess, with the aid of which the femoral head can be at least partially encompassed. The tool attachment is advantageously designed such that it is hollow-cylindrical, wherein the cylinder has an open base area which faces the femoral head for machining. The tool attachment can thus be slid over the femoral head. The at least one machining section is then for example situated on an inner surface and/or inner shell surface of said hollow-cylindrical tool attachment, in order to enable the opposite surface of the bone to be machined. The tool attachment therefore has for example the shape of a hollow cylinder comprising an open base area. It is however also possible to configure it in the shape of a cone comprising an open base area, wherein the open base area advantageously faces the femoral head for machining. In this case, a number of machining sections (at least two) lie opposite each other, not in parallel; rather, the longitudinal axes of the machining sections are at an angle with respect to each other.

The tool attachment can also comprise an inner supporting section which acts as a bearing section for the connecting section. The supporting section can be arranged in the interior (i.e. in a region which is surrounded by the movement region of the at least one machining section) and/or parallel to and/or along a longitudinal axis of the tool attachment and/or robot arm and can exhibit a linear shape. This longitudinal axis is preferably aligned with the longitudinal axis of the femoral head and/or fraising head guide, such that the two longitudinal axes and/or axes of symmetry which lie in the longitudinal direction lie one on top of the other and/or parallel to each other. This increases the stability of the arrangement of the tool attachment on the femoral head while the bone is being machined. The linear supporting section can for example be designed such that it has a cylindrical shape and/or is rod-shaped and is arranged coaxially with respect to the hollow cylinder which comprises the at least one machining section. The hollow cylinder and/or the at least one machining arm comprising the at least one machining section can be at least partially covered by the supporting section on its side facing away from the bone. The supporting section can comprise the connecting section. The supporting section thus advantageously extends in the direction of and/or parallel to a longitudinal axis of the tool attachment and/or robot arm.

Another component of the invention is a system consisting of a tool attachment as described above and a marker device, in particular a guide marker device, wherein the guide marker device can be mechanically connected to a fraising head guide, in particular to the part of the fraising head guide which is exposed after the fraising head guide has been inserted into the femoral bone (in particular, the connector piece). This system consisting of a tool attachment and a guide marker device can also comprise a surgical navigation system.

A surgical navigation system is understood to mean a system consisting of: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) comprises a processor (CPU), a working memory (RAM), advantageously an indicating facility (for example, a visual indicating facility such as a monitor and/or an audio indicating facility such as a loudspeaker) and advantageously a permanent data memory (for example, a hard drive), wherein the data processing device processes navigation data relayed to it from the receiver and can advantageously output guidance information to a user via the indicating facility. The navigation data can be stored in the permanent data memory and for example compared with data which has been previously provided in said memory.

Another component of the invention is a medical data processing method, in particular a control program for positioning a tool attachment as described above on a part of a bone, in particular a femoral head, by means of a control device, wherein the control program advantageously runs on a data processing device, in particular a computer (for example, in a processor which is assigned to a surgical navigation system), and can comprise the following steps: geometry data, in particular data comprising information on the geometry of the part of the bone to be machined, for example the femoral head, is advantageously provided—in particular, read in—by the control program, preferably within the framework of a registering method with the aid of a surgical navigation system. This geometry data can then be stored in a storage device of the computer. A longitudinal axis of the part of the bone is ascertained from the geometry data of the part of the bone. Guide data, which comprises information on the location of the guide marker device with respect to the part of the bone, in particular with respect to the longitudinal axis of the part of the bone, is also advantageously provided to the control program, wherein the position of the guide marker device is detected via a surgical navigation system. Location data which comprises information on the spatial location of the tool attachment (in particular relative to the guide marker device) is also provided to the control program. This location data can be ascertained via a marker device which is attached to the tool attachment (i.e. a tool marker device) and/or a robot marker device and/or the known relative locations between the control device and the part of the bone and between the control device and the tool attachment. A control device, in particular a robot, can then be controlled by the control program such that its work arm positions a marker device (guide marker device) on and/or parallel to the longitudinal axis. The tool attachment is also guided to the guide marker device via the control device. To this end, control data which causes the control device to guide the tool attachment to the guide marker device is provided to the control program. Such control data comprises advantageous information on the location of the tool attachment relative to the guide marker device and/or the fraising head guide. The control data can also comprise instructions which in particular indicate how the tool attachment has to be moved and/or navigated in order to be able to be coupled to the fraising head guide. The control data is advantageously determined with the aid of a data processing device which in particular forms part of the surgical navigation system, wherein the data processing device advantageously ascertains the locations and/or instructions by comparing the locations and/or positions of the tool attachment and the guide marker device and/or fraising head guide. Determining the control data can in particular be based on the guide data and the location data, wherein the control data causes the control device to guide the tool attachment to the guide marker device. The connecting section is then connected, in particular coupled, to the fraising head guide and/or the guide marker device. It is also possible to determine connection data which comprises information on whether or not the connecting section has been connected to the fraising head guide and/or the guide marker device. The connection data can in particular be determined by means of the guide data and/or location data and/or control data. Machining the bone using the tool attachment is in particular enabled when the connection data indicates the connection; before the connection is indicated, machining is in particular blocked. In the subsequent course of the method, the spatial location of the tool attachment can then be detected, once the connecting section has been connected to the fraising head guide and/or the guide marker device. This location can for example be detected in a coordinate system which was fixed with respect to the position of the tool attachment or the part of the bone before connecting.

In order to communicate the control signals between the control program and/or data processing device and the control device (which can for example comprise a robot arm), it is possible to connect the data processing device to the robot using a cable. It is however equally possible in accordance with the invention to communicate the control signals in the form of optical signals and/or radio signals. The control program then controls a control device (which can, but need not, be identical to the first control device and in any event can comprise a robot and/or robot arm), such that a tool attachment as described above can be applied to the guide marker device. This can be achieved by aligning the longitudinal axis of the tool attachment and/or robot arm (if, for example, the supporting section of the tool attachment is attached to the robot arm such that it is stationary relative to the robot arm) in a suitable position relative to the longitudinal axis of the femoral head and moving it to the femoral head and/or navigating it into a particular position relative to the femoral head (the machining position) which is suitable for fraising. It is also possible to navigate the tool attachment such that a longitudinal axis of the grinding parts (i.e. the at least one machining section) assume a particular position relative to the longitudinal axis of the femoral head, wherein the longitudinal axis of the machining section in particular lies on and/or parallel to the longitudinal axis of the femoral head in this position. The longitudinal axis of the at least one machining section is in particular the axis of rotational symmetry about which the at least one machining section is moved when machining the bone, preferably rotationally. As the tool attachment approaches the femoral head, in particular the guide marker device, the guide marker device is then inserted into the cavity and/or the tool attachment is coupled to the fraising head guide, in particular to its connector piece, by means of the connecting section.

A section of program which indicates the need to remove the guide marker device can be incorporated into the control program described above. This section of the program can advantageously be run after the tool attachment has been coupled to the fraising head guide. "Removing the guide marker device" means removing it from the femoral head and/or fraising head guide (in particular from its connector piece) and/or removing it from the working region (movement region) of the at least one machining section. The indication is advantageously output when the surgical navigation system detects the guide marker device, even though it should have been removed from its position within the working region of the at least one machining section in accordance with a predetermined program sequence, and/or detects the marker device at a position at which it is not supposed to be situated at the start of machining.

For this purpose, verification data can be ascertained by the control program which comprises information on whether at least a part of the guide marker device and/or bone marker device has been removed (in particular from the movement region of the at least one machining section). Guidance information data can also be ascertained in the control program which causes a guidance information device to output a signal (which in particular comprises the indication) which is based on the verification data.

The indication can be output to a user as a signal, for example as a visual and/or acoustic and/or tactile signal, via a guidance information device. To this end, the control program can output a signal to a visual indicating device, for example a monitor (which can be connected to the data processing device and/or the surgical navigation system). It is also possible in accordance with the invention to output a signal to an acoustic signal device, for example a loudspeaker and/or a speech module output device, which is connected to the computer and/or the surgical navigation system. The guidance information can indicate to the user that an action by the user is necessary in the corresponding program step in order to remove the guide marker device and/or the marker holders and/or reference star holder. If the guide marker device comprises the fraising head guide itself, for example by way of a material-fit connection, then at least a part of the marker device (i.e. the marker holders and/or a holding element and the marker elements, but not a fastening shaft included in the fraising head guide together with a connector piece) is removed. Guidance information can also be correspondingly output if it has been determined that the guide marker device has already been removed. The determination as to whether or not the guide marker device is situated on the fraising head guide and/or within the working region of the machining section can for example be made via an electrical signal: a voltage can be applied between the marker device and the applying facility, which indicates the presence of the marker device. The measured voltage value and/or current can be relayed to the control program as a digital measurement value for subsequent use. An analogous query and guidance information can be provided for the bone marker device, in order to likewise ensure that it has been removed from the working region before machining.

The control program described above can be stored on a computer-readable medium such as a magnetic memory (for example a floppy disk, a hard drive, a USB memory and/or a flash memory) and/or an optical storage medium (such as a CD-ROM or DVD). The computer-readable medium can then be read out on a computer, such that the control program runs on the computer.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

BRIEF DESCRIPTION OF THE DRAWINGS

FIG. 1 shows a femoral head being registered.

FIG. 2 shows the model which is based on a morphing method.

DETAILED DESCRIPTION

Figure 3A:
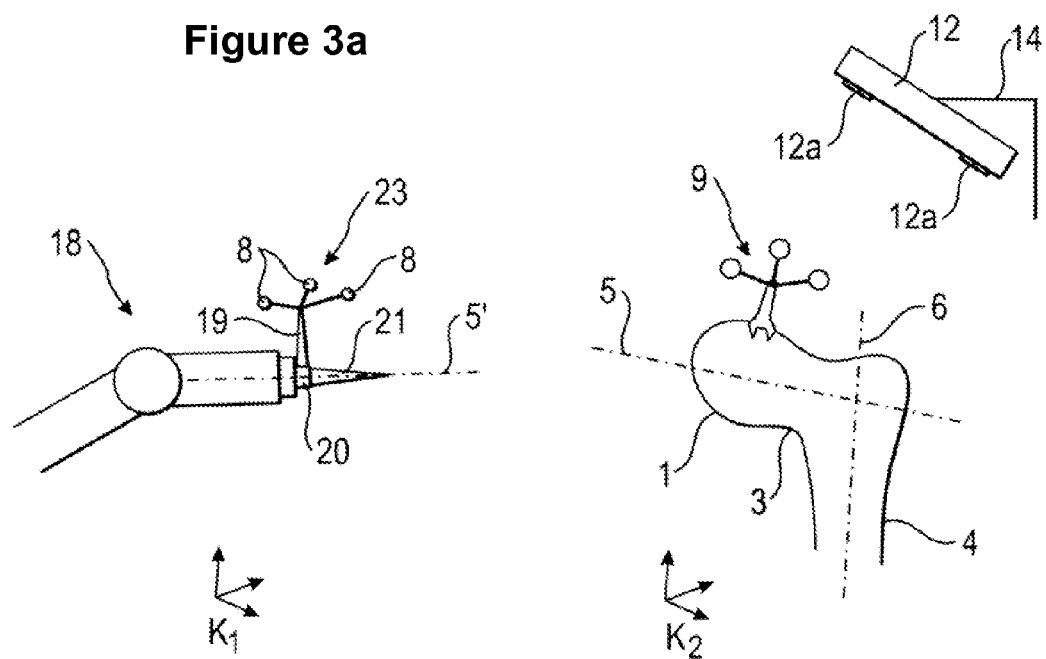
FIG. 3a shows a fraising head guide being navigated relative to a femoral head.

FIG. 1 shows a section of a femoral bone comprising a bone shaft 4, a femoral head 1 and a femoral neck 3. The femoral head 1 is to be conformed to the shape 2 to be generated (the machining shape 2) with the aid of a tool attachment 26 in accordance with the invention. The shaft 4 of the femoral bone exhibits a longitudinal axis 6; the femoral head 1 exhibits a longitudinal axis 5 which advantageously coincides with the longitudinal axis of the machining shape 2. A marker device (bone marker device) 9 comprising markers 8, marker holders 10 and a holding element 11 is attached to the femoral head 1. A pointer 7 comprising a holding grip 72 and two markers 8 is used to measure off and/or register the geometry of the original surface of the femoral head 1 which is to be machined. To this end, the tip 71 of the pointer is guided along the surface. A surgical navigation system 17 comprises: a transmitter, in particular an infrared transmitter 12; two receivers, in particular two detection devices 12a (for example, optical and/or digital cameras) which are sensitive to electromagnetic radiation, in particular infrared light; a data processing device 13 (for example, a commercially available computer comprising at least a processor, a working memory and a permanent memory); a data connection 14 (for example, a radio connection and/or a connection which communicates data with the aid of electromagnetic radiation and/or a conventional data cable) for communicating data between the transmitter 12 and the receivers 12a and the data processing device 13; an indicating device 15 (which for example comprises a CRT monitor or a TFT screen and/or an audio transmitter, for example a loudspeaker) for indicating data; and input means 16 (for example, a keyboard and/or a mouse). The surgical navigation system 17 detects the location of the markers 8 on the pointer 7. It is thus possible, when measuring off the original surface of the femoral head 1 which is to be machined within the framework of the method, to calculate a model of the surface geometry and integrate said model into the coordinate system $K_1$ which for example represents the spatial coordinate system in a treatment room and/or operating theatre.

FIG. 2 shows a screen output of a patient-specific model of a surface geometry of a femoral head which is calculated in a registering and/or morphing method. A generic bone model is adapted, with the aid of the registered points of the actual bone, to form a patient-specific bone model in a so-called morphing method, wherein FIG. 2a shows various perspectives of an exterior view of the surface model, wherein a bar 32 indicates the progress of the calculation of the model. In the scenario shown, the calculation of the surface model is 90% complete. FIG. 2b shows the screen view of a software which can run on the data processing device 13 and helps to perform the control program in accordance with the invention. The screen output 33 shows a frontal or dorsal view of a femoral head 1, in which a machining region 38 is indicated, wherein the machining region 38 represents the region of the femoral head 1 which is to be machined, in particular fraised, using the tool attachment 26 in accordance with the invention. The screen output 34 shows a frontal or dorsal view of a femoral bone 4, in which the longitudinal axis 5 of the femoral head 1 is indicated. The screen output 35 shows a basal or cranial view of a femoral head 1 and femoral neck 3, in which the longitudinal axis 5 of the femoral head 1 is indicated. The screen output 36 shows a view of the femoral head 1 along its longitudinal axis 5. The screen output 37 comprises information fields and control fields for a user. With the aid of the information fields, the user is provided with information on the perspective of the screen outputs 33, 34, 35, 36; for example, the user receives data concerning an angle at which the calculated surface model is projected. The control fields enable the user to control the screen outputs 33, 34, 35, 36, such that the perspective of the representation for the surface model can be influenced and/or changed.

FIG. 3a shows a fraising head guide—which is designed for example in this case in the form of a fastening shaft 21—being navigated relative to a femoral bone 4, in particular a femoral head 1, with the aid of a control device which in this case takes the form of a robot arm 18. While the fastening shaft 21—which comprises a connector piece 20 to which a guide marker device 23 comprising markers 8 and a holding element 19 is attached—is navigated relative to the femoral head 1, to which the bone marker device 9 described above is attached, the fastening shaft 21 is guided with the aid of a surgical navigation system 17, wherein the transmitter 12, receivers 12a and data connection 14 of the surgical navigation system 17 are shown in FIG. 3a. The robot arm 18 is then controlled with the aid of the surgical navigation system 17, such that the fastening shaft 21—the position of which is advantageously stationary and known relative to the guide marker device 23—assumes a defined location and/or position relative to the femoral head 1, the position of which can be ascertained with the aid of the bone marker device 9. In particular, the robot arm 18 is controlled such that the longitudinal axis 5' of the fastening shaft 21 is positioned parallel to and/or aligned with the longitudinal axis 5 of the femoral head 1. The longitudinal axis 5' of the fastening shaft 21 can be parallel to and/or aligned with a longitudinal axis of at least an end member of the robot arm 18 which lies directly in front of the fastening shaft 21 and/or its connector piece 20. During the movement of the fastening shaft 21 relative to the femoral head 1, different coordinate systems can be used for navigating the fastening shaft 21 and the femoral head 1. These coordinate systems can in particular be established as right-angled and/or Cartesian and/or three-dimensional coordinate systems. Thus, for example, the fastening shaft 21 can be guided in a coordinate system $K_1$ which for example has its centre point and/or origin at a location which lies in a component of the robot arm 18 or the guide marker device 23 or the connector piece 20 or the fastening shaft 21. The fastening shaft 21 is then navigated by calculating the position of the fastening shaft 21 in the coordinate system $K_1$ relative to for example the receivers 12a of the surgical navigation system 17, wherein the position of the fastening shaft 21 and/or the location of its longitudinal axis 5' is advantageously known in the coordinate system $K_1$, in particular relative to the origin of the coordinate system $K_1$. Similarly, the bone shaft 4 and/or the femoral head 1—as a component of the femoral bone 4—can be navigated in a coordinate system $K_2$ which has its centre point and/or origin at a location which is encompassed by a component of the bone shaft 4 or the femoral neck 3 or the femoral head 1 or the bone marker device 9. The femoral head 1 is then for example navigated in the coordinate system $K_2$ by detecting the location of the femoral head 1 relative to the receivers 12a of the surgical navigation system 17, wherein the position of the femoral head 1 and/or the location of its longitudinal axis 5 is advantageously known in the coordinate system $K_2$, in particular relative to the origin of the coordinate system $K_2$. Once the fastening shaft 21 has been inserted into the femoral head 1, both the femoral head 1 and/or bone 4 and the fastening shaft 21 and/or the robot arm 18 can be navigated with the aid of the guide marker device 23 only, wherein the positions and/or locations of both the femoral head 1 (femoral bone 4) and the fastening shaft 21 and/or robot arm 18 can be given in a common coordinate system which can be based on the coordinate system $K_1'$ or the coordinate system $K_2'$.

Figure 3B:
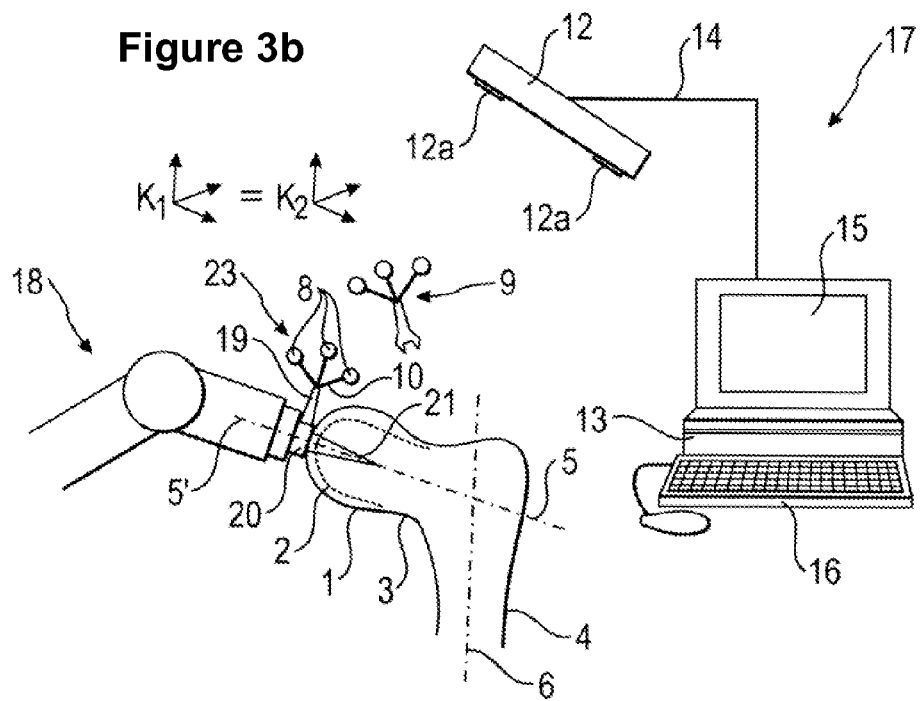
FIG. 3b shows a fraising head guide being inserted into a femoral head with the aid of a control device and a surgical navigation system.

FIG. 3b shows the fastening shaft 21 still fastened to the robot arm 18 and already inserted into the femoral head 1, wherein the guide marker device 23 is still situated on the connector piece 20. Since the fastening shaft 21 and the femoral head 1 are then fixedly connected to each other, for example via a screw mechanism and/or a positive-fit and/or force-fit connection between the fastening shaft 21 and the femoral head 1, the fastening shaft 21 and the femoral head 1 can then be navigated in a common coordinate system, wherein the position of both the femoral head 1 and the connector piece 20 and/or fastening shaft 21 is advantageously known relative to the origin of the common coordinate system. Only a guide marker device 23 is then still necessary in order to navigate the two parts, such that the bone marker device 9 can be removed from the femoral head 1. FIG. 3b likewise shows how the longitudinal axis 5' of the fastening shaft 21 can be aligned with the longitudinal axis 5 of the femoral head 1. Once the fastening shaft 21 has been inserted into the femoral head 1, the robot arm 18 can be removed from the fastening shaft 21 and/or its connector piece 20. It is expedient to leave the guide marker device 23 still fastened to the connector piece 20, in order that the tool attachment can subsequently be navigated relative to the guide marker device 23 (in a similar way to navigating the fastening shaft 21 relative to the femoral head 1).

Figure 4:
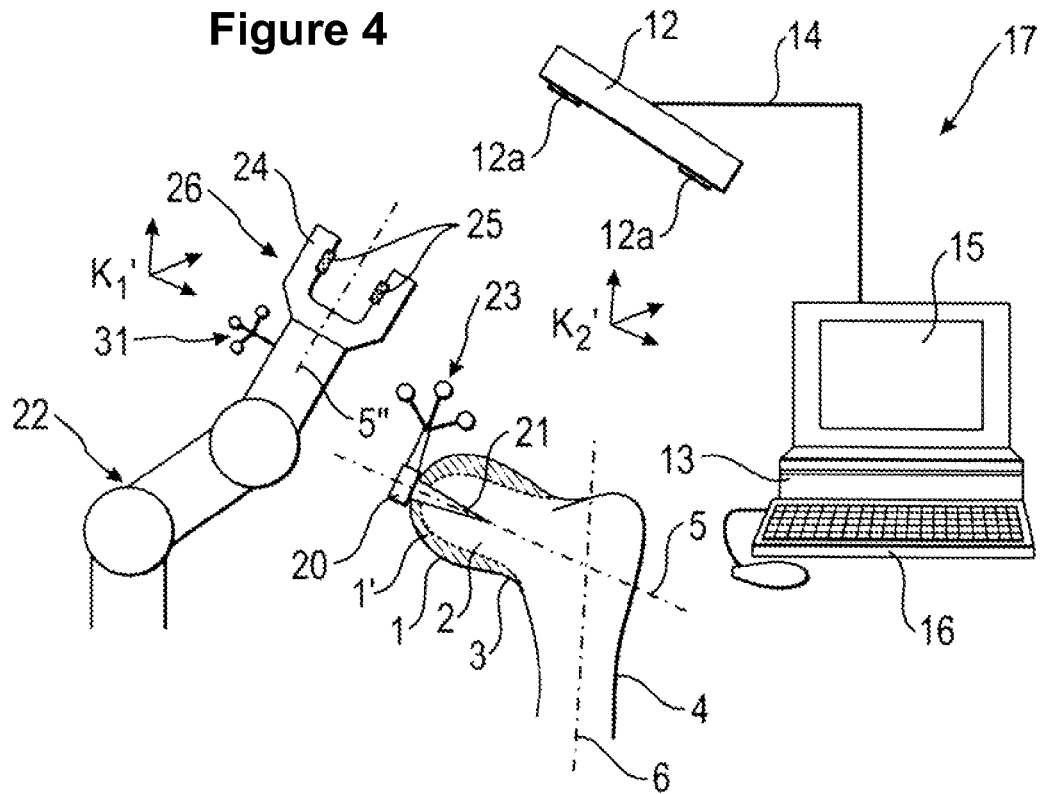
FIG. 4 shows a tool attachment in accordance with the invention, which is fastened to a control device, being navigated relative to a fraising head guide which is fastened in a femoral head.

FIG. 4 shows a fastening shaft 21 which is inserted into the femoral head 1 and has a guide marker device 23 attached to its connector piece 20. A tool attachment 26 can then be navigated with the aid of a surgical navigation system 17 relative to the connector piece 20, the position of which relative to the guide marker device 23 is advantageously stationary and known, wherein the tool attachment 26 is advantageously attached to a robot arm 22 which can be identical to the robot arm 18 or can also represent a different robot arm. A marker device (robot marker device) 31 is advantageously attached to the robot arm 22, wherein the position of the tool attachment 26 relative to the robot marker device 31 is in particular known. Another marker device (tool marker device) 31 can additionally or alternatively be attached to a part of the tool attachment 26, wherein the position of the tool attachment 26 is also then advantageously stationary and known relative to the tool marker device 31. The robot arm 18, 22 can be navigated with the aid of a robot marker device 31 and/or a tool marker device 31. It is however also possible in accordance with the invention to navigate the robot arm 18, 22 merely with the aid of the prior-known dimensions of the robot arm 18, 22 and/or knowledge of the location of its components relative to a prior-known location in the reference system $K_1$ and/or $K_1'$. In the latter case, it is possible to dispense with a robot marker device 31 and/or tool marker device 31 for navigating the robot arm 18, 22 and/or tool attachment 26. The tool attachment 26 comprises a supporting section 24 which advantageously has a rotationally symmetrical shape. The supporting section 24 can thus exhibit a forcipate shape, as explained above, or can also be designed in the form of a hollow cylinder, wherein an opening is advantageously situated in the supporting section in the direction of a side of the tool attachment 26 which faces away from the robot arm 22, such that the supporting section 24 can be positioned around a femoral head 1 and/or a femoral head 1 can be inserted into the interior of the supporting section 24. At least one machining section 25 is arranged on the supporting section 24, wherein the machining section 25 can in particular comprise a drill and/or a fraise. In the case of a fraise, the machining section 25 is in particular configured to machine and/or fraise and/or remove the shaded machining region 1' of the femoral head 1, such that a machining shape 2 of the femoral head, which in particular exhibits an elementary cylindrical shape but can also be tapered and/or conical towards the end of the femoral head (i.e. the end which anatomically points towards the hip joint socket), is generated. The tool attachment 26 is in turn moved and/or navigated relative to the femoral head 1 and/or connector piece 20 with the aid of a surgical navigation system 17, in a similar way to navigating the robot arm 18 and/or fastening shaft 21 relative to the femoral head 1, as shown in FIGS. 3a and 3b and explained above, wherein the position of the femoral head 1 relative to the guide marker device 23 is advantageously stationary and known. The robot arm 22 and/or tool attachment 26 can be guided in a coordinate system $K_1'$ which is different from the coordinate system $K_2'$ in which the femoral head 1 and/or connector piece 20 is guided. The coordinate systems $K_1'$ and $K_2'$ can in turn be established as right-angled and/or Cartesian and/or three-dimensional coordinate systems. The origin of the coordinate system $K_1'$ can lie at a location which is encompassed by a component of the tool attachment 26 or the robot arm 22 or a robot marker device 31 or tool marker device 31. The origin of the coordinate system $K_2'$ can lie at a location which is encompassed by the femoral head 1 or the fastening shaft 21 or the machining shape 2 or the femoral shaft 4 or the guide marker device 23 or the connector piece 20. The location and/or position of the tool attachment 26 relative to the origin of the coordinate system $K_2'$ is advantageously known. The location and/or position of the femoral head 1 and/or connector piece 20 relative to the origin of the coordinate system $K_1'$ is advantageously known. The tool attachment 26 is advantageously navigated and/or moved relative to the femoral head 1 and/or connector piece 20 in such a way that the longitudinal axis 5" of the tool attachment 26 is positioned parallel to and/or aligned with the longitudinal axis 5 of the femoral head and/or the fastening shaft 21, wherein the longitudinal axis 5" of the tool attachment 26 can be parallel to and/or aligned with a longitudinal axis of at least an end piece of the robot arm 22 which is arranged directly in front of the tool attachment 26. Once the tool attachment 26 has been coupled to the fastening shaft 21, both the tool attachment 26 and the fastening shaft 21 can be navigated with the aid of the guide marker device 23 only, wherein the navigation can be performed in such a way that the positions and/or locations of both the tool attachment 26 and the fastening shaft 21 are determined in a common coordinate system which can be based on the coordinate system $K_1'$ or the coordinate system $K_2'$.

Figure 5:
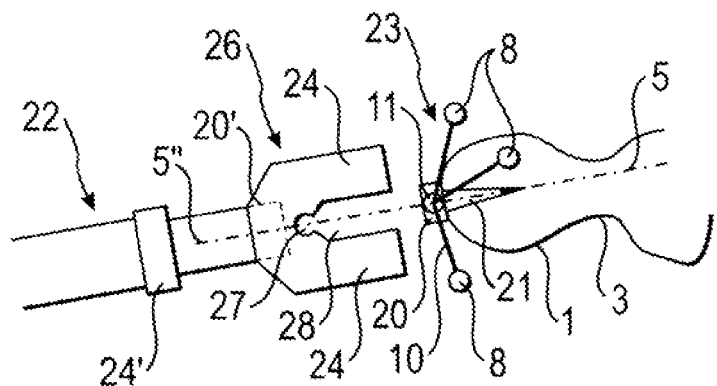
FIG. 5 shows a tool attachment in accordance with the invention, with a coupling facility arranged on it.

FIG. 5 shows a perspective view in the basal or cranial direction of the femoral head 1 with a fastening shaft 21 inserted into it. A guide marker device 23 comprising markers 8 and marker holders 10 is attached to the connector piece 20 of the fastening shaft 21. The tool attachment 26, which is situated on a robot arm 22, is then aligned such that its longitudinal axis 5" is aligned with the longitudinal axis 5 of the femoral head 1 and/or fastening shaft 21. The tool attachment 26 comprises a cavity 28 in the form of a slot (which in particular lies on and/or parallel to an axis of rotational symmetry and/or a longitudinal axis and/or in a plane which runs parallel to such an axis). Said cavity 28 is arranged between and/or in parts of the supporting section 24. If the supporting section 24 is designed in a forcipate shape, the cavity 28 is situated between the forcipate arms of the supporting section 24. The cavity 28 exhibits the shape of a slot and is open on a side which advantageously faces away from the robot arm 22 and, in the position shown, points in particular towards the connector piece 20, in order to enable a holding element 11 or other part of a guide marker device 23 to be inserted into the tool attachment 26, wherein the holding element 11 and/or other part of a guide marker device 23 can be guided as far as the end of the cavity 28 which faces the robot arm 22 and inserted into an engaging element 27. The engaging element 27 can in particular be embodied to be round or also polygonal and can ensure that the tool attachment 26 is seated on the holding element and/or guide marker device 23 in a positive fit and/or in a force fit and/or in an exact fit. If the guide marker device 23 is not attached to the connector piece 20 or arranged at a location of the femoral head 1 which is covered by a supporting section 24 and/or machining section 25, a probe can be provided on the tool attachment 26 which enables a mechanical and stationary, in particular force-fit and/or positive-fit connection between the tool attachment 26 and the guide marker device 23. The cavity 28 can then for example be arranged on the probe in the form of a slot. The tool attachment 26 also comprises a connecting section 20' which can enter into a stable mechanical, in particular positive-fit and/or force-fit connection with the connector piece 20. The fastening facility 24' serves to connect the tool attachment 26 to the robot arm 22.

Figure 6:
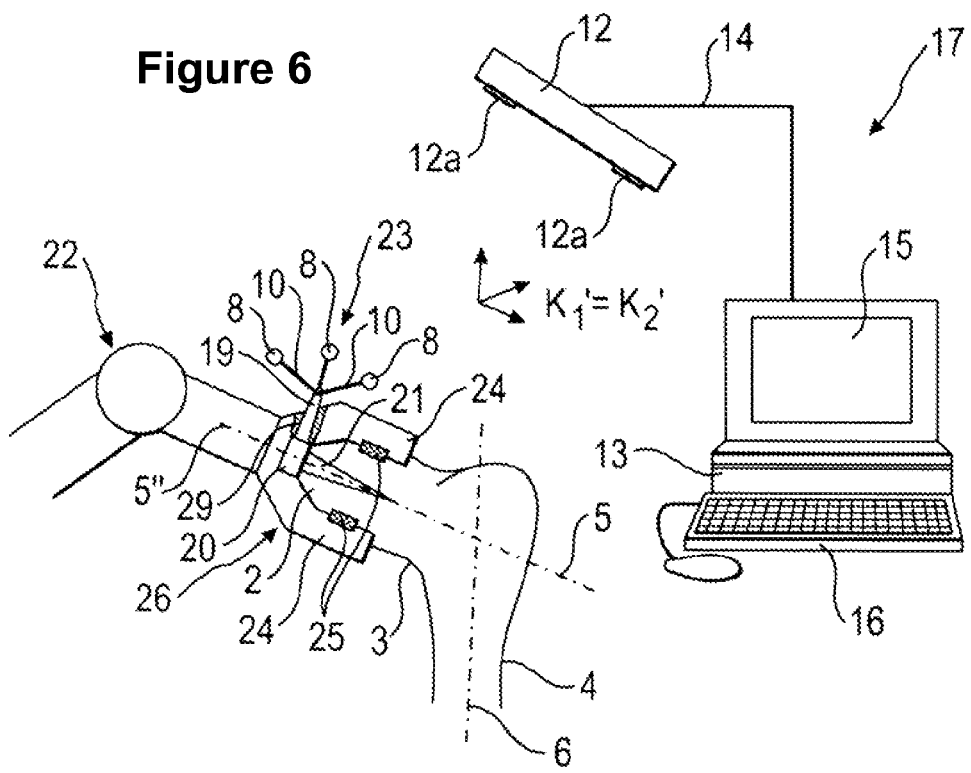
FIG. 6 shows a tool attachment in accordance with the invention which is situated in a machining position on a femoral head.

FIG. 6 shows the tool attachment 26 applied to a femoral head 1, wherein the connector piece 20 engages with a connecting section of the tool attachment 26 and is advantageously arranged on the longitudinal axis 5" of the tool attachment 26. The mechanical connection between the connector piece 20 and the connecting section can be designed in a positive fit and/or in a force fit. The supporting section 24 girdles the femoral head 1 in such a way that the machining sections 25 at least partially abut and/or lie opposite the machining region 1'. The engaging element 27 is advantageously arranged such that it encompasses the guide marker device 23 when the tool attachment 26 is situated in a machining position in the femoral head 1.

Figure 7:
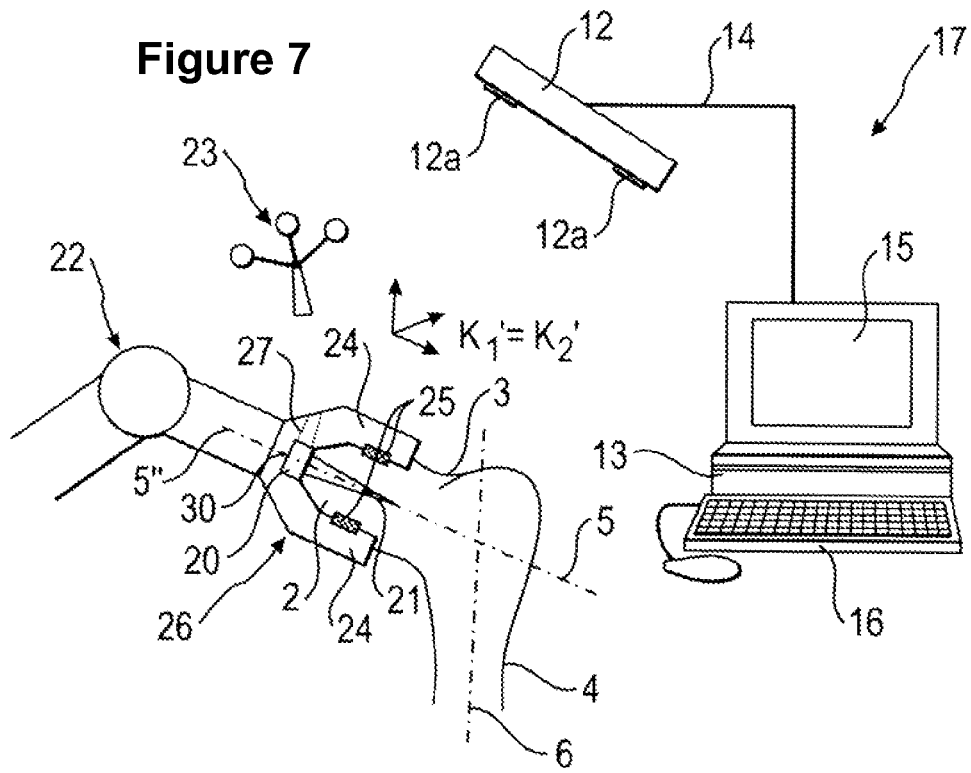
FIG. 7 shows a tool attachment in accordance with the invention which is situated in a machining state on a femoral head.

FIG. 7 shows the guide marker device 23 being removed from the tool attachment 26 in order to machine the machining region 1'. The tool attachment 26 is therefore situated in a machining position, i.e. in its machining configuration, it has assumed a position on the part of the bone to be machined which is suitable for machining, wherein an opening in the tool attachment 26, which is in particular formed by the engaging element 27, remains available. It is however also possible in accordance with the invention to then seal the engaging element 27 such that no particles can pass from the outside into the interior of the tool attachment 26 and/or onto the connecting part 20. The engaging element 27 can for example be sealed using a cap made of a plastic or metal, which is placed onto the opening of the engaging element 27 from the outside in a positive fit and/or in a force fit. In a similar way, it is possible to seal the slot of the cavity 28 before the machining region 1' is machined. It is thus for example possible to reduce and/or avoid contamination of the working region when the machining sections 25 and/or the supporting section 24 are moved and/or rotated. The supporting section 24 can remain stationary relative to the robot arm 22 and/or femoral head 1 while the machining region 1' is machined; it can however also be moved relative to the robot arm 22, in particular rotated about its longitudinal axis 5", in order to enable the machining region 1' to be rotationally fraised. In this case, it is advantageous to remove the guide marker device 23 before machining the bone, in order to avoid damage to the tool attachment 26 and/or the guide marker device 23. In this case, it is possible to leave the guide marker device 23 in its location, i.e. in particular on the connector piece 20 and/or on the engaging element 27. This is primarily possible when the guide marker device 23 is situated in said position outside a movement region of parts of the tool attachment 26 which are moved in order to machine the surface of the bone (i.e. in particular outside the movement region of the machining sections 25).

Figure 8:
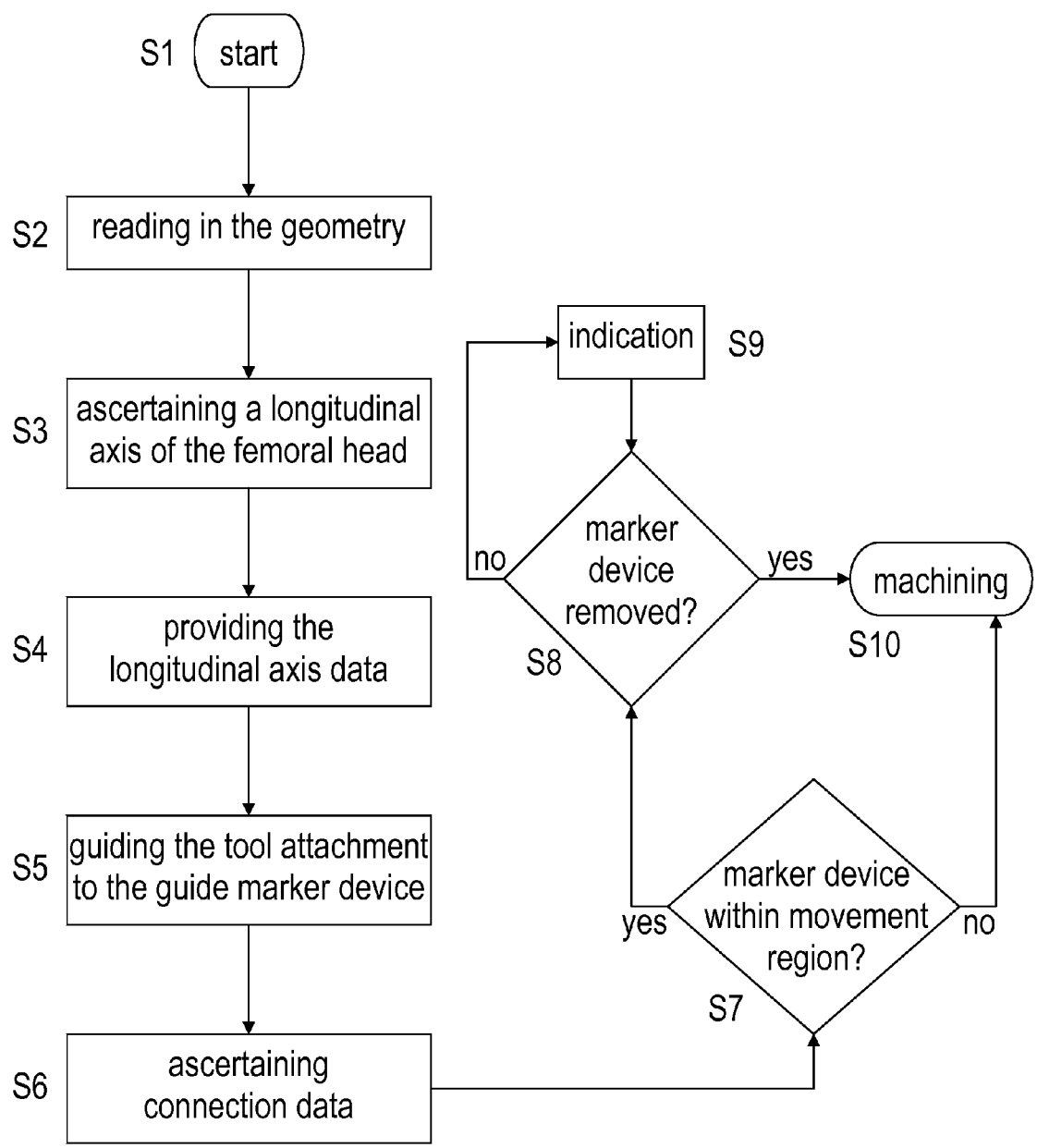
FIG. 8 shows a flow diagram of a control program in accordance with the invention for controlling the tool attachment.

FIG. 8 shows a flow diagram for the data processing method in accordance with the invention, i.e. the control program for positioning a tool attachment 26 as described above on a part of a bone, in particular a femoral head 1, by means of a control device, wherein the control device can comprise a surgical navigation system 17 and/or a robot arm 18, 22. In a step S1, the program is started, for example called up by a data processing device 13. Firstly, the geometry of the femoral head 1 is read in, in particular with the aid of a registering method, in a step S2. It is however also possible to use geometry data from an imaging method (in particular MRT or CT). A longitudinal axis 5 of the femoral head 1 is ascertained from the geometry of the femoral head and/or from the ascertained model of the femoral head. A guide marker device 23 can then be attached on the longitudinal axis 5 of the femoral head 1 using a robot arm 18. This guide marker device 23 can in particular be attached on a connecting part 20 of a fastening shaft 21. The guide marker device 23 can however also be attached at another point on the femoral head which advantageously lies in a stationary and known location relative to a fastening shaft 21 which is inserted into the femoral head 1 and/or relative to its connector piece 20. In a step S4, longitudinal axis data is provided which describes the relative location between the guide marker device and the longitudinal axis 5. The tool attachment 26 is then navigated relative to the guide marker device 23, in particular guided to it, in a step S5. To this end, the location data described above is in particular provided to the control program. In step S6, the control program ascertains connection data which in particular includes information on whether the tool attachment 26 (in particular its connecting section 20') is mechanically connected to the fastening shaft 21 and/or the guide marker device 23. The control program can also be provided, in particular by the surgical navigation system 17, with type data which includes information on the type of the tool attachment 26 being used. This can for example be achieved by providing a magnetic data memory in the tool attachment 26, which has the corresponding information stored on it and can be read out by the data processing device 13 via the robot arm 22. To this end, the robot arm 22 is connected to the data processing device 13 via a data connection 14. The data processing device 13 can read out data from the magnetic memory which comprises information on the type of the tool attachment and its operational properties and/or geometry. As applicable, the data processing device 13 can also receive only data concerning the type of the tool attachment and compare it with a data set, which is stored in the permanent memory of the data processing device 13, concerning the type of the tool attachment 26. This comparison can provide a result which includes information on the operational properties, such as for example the movement region of a machining section 25 when the machining region 1' is being machined. This data can be compared with the position of the guide marker device 23 as detected by the surgical navigation system 17. In a step S7, a verification is correspondingly made as to whether the guide marker device 23 is situated within the movement region of a part of the tool attachment 26 (in particular, a machining section 25) which is moved in order to machine the machining region 1'. If this is not the case, the machining region 1' continues to be machined in a step S10. If, however, the marker device is situated within the movement region in accordance with Step S7, then a verification is made in a step S8 as to whether the guide marker device 23 has been removed from the movement region, i.e. verification data is ascertained which comprises information on whether at least a part of the guide marker device 23 and/or the bone marker device 9 has been removed and/or as to whether no part of the guide marker device 23 and/or the bone marker device 9 is still situated within the movement region. The verification data can in particular be ascertained from a comparison of the location of the guide marker device 23 and/or bone marker device 9 and the location of the tool attachment 26. On the basis of the verification data, a decision is then made in a step S10 as to whether the part of the bone 1 can begin to be machined. The verification data can also be ascertained in such a way that a user makes a manual input into the data processing device which relays to the data processing device information as to whether or not the guide marker device 23 has been removed from the movement region. This input can then simplify ascertaining the verification data, by making the comparison of the locations of the tool attachment 26 and the guide marker device 23 and/or bone marker device 9 dispensable. If the guide marker device 23 has been removed from the movement region, a machining region 1' continues to be machined in a step S10. If the result of step S8 is negative, i.e. if the guide marker device 23 has not been removed from the movement region, an indication is made to a user in a step S9 that the guide marker device 23 is situated within the movement region. This indication can for example be made in a visual form on an output device 15; it is however also possible in accordance with the invention to output the indication as an audio signal (for example as a speech output or a simple acoustic warning signal). Once the indication has been output, the control program returns to step S8, in which another verification is made as to whether the guide marker device 23 has since been removed from the movement region. The decision in accordance with Step S8 as to whether the guide marker device 23 has been removed from the movement region can be made by comparing the position of the guide marker device 23 as detected by the surgical navigation system 17 and the operational properties of the tool attachment 26 as ascertained in Steps S6 and S7. If the guide marker device 23 is not in the movement region ("no" in step S7) or the guide marker device has been removed from the movement region ("yes" in step S8), it is possible to begin machining in a step S10.

Control of the tool attachment 26 can then be released by the control program. The decision as to whether or not the tool attachment 26 is released can in particular be based on the result of step S8, wherein "releasing" the tool attachment 26 is in particular understood to mean that the tool attachment 26 no longer receives, from the control program, any control signals which influence its spatial position. It is however possible in accordance with the invention for control signals which enable a spatially restricted movement and/or change in location of the tool attachment to continue to be transmitted to the tool attachment 26. This ensures that the tool attachment can minimally change its position—in particular, resonate—during machining, in order to avoid and/or reduce the likelihood of increased mechanical stress and thus damage to the part of the bone 1. The tool attachment 26 can however also be released in such a way that its ability to change location is only then restricted by the geometric dimensions of the robot arm 22, in particular its freedom of movement. Advantageously, however, control signals which cause an active change in location, in particular a change in location which may be traced back to a drive of the robot arm 22, are no longer transmitted to the robot arm 22 in this method step. A passive control signal which is transmitted to the tool attachment 26 is in particular understood in this context to mean a control signal which is not emitted until the tool attachment 26 assumes a particular location and/or performs a particular movement pattern. A passive control signal is thus emitted as a response to a movement and/or change in location of the tool attachment 26 and/or in response to forces which act on the tool attachment 26 and/or robot arm 22 and have been detected (for example using an acceleration sensor, a pressure sensor or a force sensor) and supplied to the control program as detection signals, and in particular causes the robot arm 22 to not (completely) suppress or block this movement and/or change in location, in order to minimize, reduce or completely suppress forces between the part of the bone 1 and the tool attachment which are generated by the movement. A movement of the tool attachment 26 and/or forces acting on the tool attachment 26 and/or the robot arm 22 are in particular counteracted. The movement and/or forces can thus be damped.

Lastly, machining data and/or machining signals can be transmitted to the tool attachment 26 which include information that the part of the bone 1 has begun and/or is to begin to be machined, in particular fraised. These signals and/or data advantageously have the form of a pulse which initiates a drive pattern, in particular a predetermined drive pattern, of the at least one machining section 25. The machining data can however also include other information, for example information on the force and/or speed with which the part of the bone 1 is to be machined and/or the pattern within which the part of the bone 1 is to be machined. Thus, the machining data in particular causes the tool attachment 26 to begin machining the part of the bone 1. In particular, the machining data does not indicate that machining has begun until the verification data indicates that the guide marker device 23 and/or the bone marker device 9 have been removed and/or the connection data indicates a connection between the tool attachment 26 and the tool attachment guide 21.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A medical system for machining a part of a bone, comprising:
    a tool attachment guide including: a fastening shaft configured to be fixedly inserted into the bone; and a trackable reference device coupled to the fastening shaft by a connecting device, wherein the trackable reference device is removably attachable to the connecting device; and
    a tool attachment, including
      i. a supporting section,
      ii. at least one machining section attached to the supporting section, the at least one machining section configured to machine the part of the bone,
      iii. connecting section attached to the supporting section and configured to fasten the supporting section to the connecting device of the tool attachment guide, and
      iv. a cavity configured to receive the trackable reference device, wherein the trackable reference device is removably attachable to the tool attachment guide through the cavity of the tool attachment.

2. The system according to claim 1, wherein the tool attachment is a tool attachment for fraising a part of a bone.

3. The system according to claim 2, wherein the part of the bone is a femoral head.

4. The system according to claim 1, wherein the cavity is configured to accommodate the trackable reference device in order to enable the connecting section of the supporting section to be connected to the tool attachment guide such that the connecting section is stationary relative to the tool attachment guide.

5. The system according to claim 4, wherein at least one of the supporting section and the machining section comprises the cavity.

6. The system according to claim 4, wherein the cavity assists in a connection between the tool attachment and the trackable reference device.

7. The system according to claim 4, wherein the cavity comprises an engaging element which assists in a mechanical connection between the tool attachment and the trackable reference device.

8. The system according to claim 1, wherein the supporting section is rotationally symmetric.

9. The system according to claim 1, further comprising a surgical navigation system.

10. A medical system for machining a part of a bone, the system comprising:
    a. a tool attachment guide including: a fastening shaft configured to be fixedly inserted into the bone; and a trackable reference device coupled to the fastening shaft by a connecting device, wherein the trackable reference device is removably attachable to the connecting device; and
    b. a tool attachment, including
      i. a supporting section,
      ii. at least one machining section attached to the supporting section, the at least one machining section configured to machine the part of the bone,
      iii. connecting section attached to the supporting section and configured to fasten the supporting section to the connecting device,
      iv. a first cavity configured to receive the tool attachment guide, the first cavity having a longitudinal axis extending along a length of the first cavity, and
      v. a second cavity through which at least part of the trackable reference device can be guided, the second cavity having a longitudinal axis extending along a length of the second cavity, wherein the longitudinal axis of the first cavity is non-parallel to the longitudinal axis of the second cavity.

11. The system according to claim 10, wherein the supporting section is rotationally symmetric.

* * * * *